United States Patent [19]

Yee et al.

[11] Patent Number: 4,786,396
[45] Date of Patent: Nov. 22, 1988

[54] ION ELECTRODE AND METHOD OF MAKING IT

[75] Inventors: Sinclair S. Yee, Seattle; Hong Jin, Mill Creek; Lawrence K. Lam, Seattle, all of Wash.

[73] Assignee: The Washington Technology Center, Seattle, Wash.

[21] Appl. No.: 67,513

[22] Filed: Jun. 26, 1987

[51] Int. Cl.$^4$ ............... G01N 27/30; G01N 27/36
[52] U.S. Cl. ................... 204/420; 204/416; 204/417; 204/418; 204/435
[58] Field of Search ................ 357/25; 204/435, 416, 204/417, 418, 420, 419

[56] References Cited

U.S. PATENT DOCUMENTS

| | | | |
|---|---|---|---|
| 2,925,370 | 2/1960 | Rohrer | 204/435 |
| 3,025,174 | 3/1962 | Simon | 501/72 |
| 3,294,662 | 12/1966 | Matlow | 204/416 |
| 3,445,363 | 5/1969 | Simon et al. | 204/420 |
| 3,562,129 | 2/1971 | Simon | 204/416 |
| 3,647,666 | 3/1972 | Simon et al. | 204/416 |
| 3,671,413 | 6/1972 | Wise | 204/417 |
| 4,388,167 | 6/1983 | Ono et al. | 204/420 |
| 4,508,613 | 4/1985 | Busta et al. | 204/418 |
| 4,512,870 | 4/1985 | Kohara et al. | 204/416 |
| 4,592,824 | 6/1986 | Smith et al. | 204/416 |

OTHER PUBLICATIONS

G. Barthold et al., IBM Tech. Disclosure Bulletin, vol. 19, No. 4, pp. 1293-1294, Sep. 1976.
Urs Oesch et al., "Ion-Selective Membrane Electrodes for Clinical Use", *Clinical Chemistry*, vol. 32, No. 8, 1986, pp. 1448-1459.
R. L. Smith et al., "An Integrated Sensor for Electrochemical Measurements", *IEEE Transactions on Biomedical Engineering*, vol. BME-33, No. 2, Feb. 1986, pp. 83-90.
R. L. Smith et al., "A Solid State Miniature Reference Electrode", *IEEE Symposium on Biosensors*, 1984, pp. 61 & 62.

Primary Examiner—G. L. Kaplan
Attorney, Agent, or Firm—Christensen, O'Connor, Johnson & Kindness

[57] ABSTRACT

A liquid junction electrode 10 formed from a silicon body 14 and having a glass membrane 22 attached thereto. A reference electrode is constructed by forming the glass membrane 22 from porous glass having a preferable pore size in the range of 40 angstroms to 75 angstroms. The porous glass membrane 22 has a coating 24 of glass containing mobile ions that is electrostatically bonded to the silicon body 14. Alternatively, a glass plug 92 is formed from a paste of ground glass and organic binder that is heated to cause formation of pores and bonding of the glass plug 92 to a silicon body 94. An ion-sensitive electrode is constructed by forming the membrane 52 from an ion-sensitive glass or by filling the pores of the porous glass membrane 22 with an ion-sensitive material.

32 Claims, 6 Drawing Sheets

ION ELECTRODE AND METHOD OF MAKING IT

TECHNICAL FIELD

This invention pertains to ion electrodes for detecting ionic concentrations and a method of manufacturing the same.

BACKGROUND OF THE INVENTION

Liquid junction ion electrodes are used to detect the activity or concentration of a specific ion contained in a test solution. A typical pH meter will use a pair of electrodes. One of the electrodes is a reference electrode, and the other electrode is an ion-sensitive electrode that chemically reacts with a specific ion in the test solution. When the electrodes are immersed in the test solution, the resulting chemical reaction creates a measurable electrical potential across the two electrodes that is displayed on the meter.

Typical liquid junction reference electrodes consist of a closed glass tube having a porous glass plug at one end. An electrical conductor passes through the glass tube to make electrical contact with a reference solution that fills the interior of the glass tube. Although these conventional glass reference electrodes have functioned well, their large size and expense make them incompatible for applications utilizing the recently developed ion-sensitive field effect transistor, known as an ISFET. The unavailability of suitable miniature ion electrodes has restricted the appilcation of the ISFET as a viable chemical sensor in the industrial and biomedical fields.

Recent attempts have been made to manufacture miniaturized liquid junction reference electrodes using semiconductor fabrication techniques. One method is described by Smith et al. in "A Solid State Miniature Reference Electrode," IEEE NSF Symposium on Biosensors -- 1984, pages 61-62 (1984), and in "Integrated Sensor for Electromechnical Measurements," IEEE Transactions on Biomedical Engineering, Vol. BME 33, No. 2, pages 83-89, Feb. 1986, wherein a cavity housing a solution in a silicon base is covered with a porous silicon membrane. The major drawback to this configuration, as indicated in the above-referenced publications, is the lack of control over the pore size and density of the silicon membrane, resulting in erratic electrode performance. Another difficulty encountered in the manufacture of these silicon-based electrodes is achieving a leak-proof bond between the membrane and the silicon body.

Attempts have also been made to develop a solid state reference electrode using parylene coating on the gate of the ISFET, or using a thin-film silver/silver-chloride electrode that is either in direct contact with a test solution of a chloride ion or is covered with a polymer saturated with a chloride ion. In practice, these electrodes have failed to perform as well as the conventional glass liquid junction electrodes because of limited useful ranges in the primary ion concentrations and instability in the electrode potential due to changing concentration of the primary ion. The present invention overcomes these and other disadvantages in the manufacture and application of miniaturized silicon-based liquid junction reference electrodes. The present invention can also be employed in the manufacture of liquid junction ion-sensitive electrodes.

SUMMARY OF THE INVENTION

In accordance with the present invention, an ion electrode for detecting the ionic activity and concentration in a liquid is provided. The reference electrode comprises a body formed of silicon having a cavity that opens into an exterior surface of the body. A glass membrane, formed from a porous glass material, is attached to the body to substantially cover the cavity opening. A chemical solution fills the cavity to be in contact with the glass membrane, and an electrical conducting means passes through the body between the cavity and the exterior of the body for making electrical contact with the solution.

In accordance with another aspect of the present invention, the glass membrane is partially coated with a glass containing mobile ions that are electrostatically bonded to the body.

In accordance with another aspect of the present invention, the cavity opens to two surfaces of the body, one of the openings is covered by the glass membrane and the other opening is covered with an electrically nonconductive cover. Preferably the electrical conducting means passes through the electrically nonconductive cover.

In accordance with still another aspect of the present invention, a channel is formed in the body for filling the cavity with the solution.

In accordance with a further aspect of the present invention, the glass membrane has the pores filled with an ion-sensitive material to form a liquid junction ion-sensitive electrode.

In accordance with a method of manufacturing a reference electrode, a cavity is created in a silicon body that opens to an exterior surface of the body. Preferably the cavity is created by a chemical etching process. A small passageway is formed in the body between the cavity and the exterior of the body. The opening is covered with a glass membrane formed of porous material having a pore size in the range of 40 angstroms to 75 angstroms. The cavity is filled with a solution through the small passageway, and an electrical conductor is then passed through the small passageway to make contact with the solution.

In accordance with a further aspect of manufacturing the present invention, the opening is covered with a glass membrane formed from a porous glass material having the pores filled with an ion-sensitive material and is partially coated with a glass containing mobile ions to form an ion-sensitive electrode. Preferably the coating is applied by a sputtering process.

In accordance with another aspect of the present invention, the cavity is created by first chemically etching a first cavity from a first side of the body, then chemically etching a second cavity from a second side of the body, the second cavity communicating with the first cavity to create a larger single cavity. The first of the openings is covered with the glass membrane and the second of the openings is covered with an electrically nonconductive cover.

In accordance with another aspect of the present invention, the step of covering one of the openings with the glass membrane further comprises grinding the glass material to a powder form and combining that with an organic binder to form a glass paste. The glass paste is then applied to substantially fill the first cavity and the organic binders are evaporated out of the glass paste to form a porous glass plug that substantially seals the opening of the first cavity.

In accordance with an alternative method of manufacturing the ion electrode of the present invention, a first cavity is created in the interior of the body by chemically etching from a first side of the body. The opening of the first cavity is then sealed by appying a glass paste consisting of a mixture of ground glass material and organic binder. The organic binder is then evaporated out of the glass paste to form a glass plug that substantially seals the opening of the first cavity. A second cavity is created in the interior of the body that opens to a second side of the body by chemically etching. The second cavity communicates with the first cavity to create a larger single cavity. The larger single cavity is then filled with a solution and the opening to the second cavity is then covered with an electrically nonconductive cover having an electrical conductor passing through it to contact the solution.

As will be readily appreciated from the foregoing description, a liquid junction reference electrode formed in accordance with the present invention can be manufactured in a miniature size. This permits the liquid junction reference electrode to be integrated with ISFET circuitry. In addition, the electrode structure is more rugged and much more economical to fabricate because the modern silicon processing technology can be employed for the fabrication process. As a result, liquid junction reference electrodes of the present invention can be fabricated by batch process. In addition, the manufacturing process is applicable to the liquid junction ion-sensitive electrode as well as to the liquid junction reference electrode. Finally, ion-sensitive electrodes and reference electrodes formed in accordance with the present invention will have uniform operating characteristics that substantially match that of conventional liquid junction glass electrodes.

DETAILED DESCRIPTION OF THE PREFERRED EMBODIMENT

FIGS. 1–5 illustrate alternative embodiments of silicon-based liquid junction electrodes formed in accordance with the present invention. In the embodiment shown in FIGS. 1A and 1B, a cavity 12 is formed in a body 14 that opens to an exterior surface 16 of the body 14. Preferably the body 14 is formed of silicon, although other materials adaptable to the planar etching process are suitable. As shown in FIG. 1A, the cavity 12 has a trapezoidal cross-sectional shape wherein the walls 18 converge to the interior of the body 14. A channel 20 is formed in one of the walls 18 between the cavity 12 and the exterior surface 16.

Affixed to the exterior surface 16 is a glass membrane 22. In the embodiment illustrated in FIG. 1A, a reference electrode is formed by using porous glass for the glass membrane 22. To provide a leak-proof seal with the silicon body 14, the glass membrane 22 is partially coated with a coating 24 of glass containing mobile ions that is then electrostatically bonded to the silicon body 14. A window 26 is formed by the uncoated portion of the glass membrane 22. The window 26 provides an area for the interaction of the test solution with a primary solution 28 that fills the cavity 12. An electrical conductor 30 is passed through the channel 20 to make contact with the primary solution 28. When the ion electrode 10 is assembled, the electrical conductor 30 will be sealed in the channel 20 to prevent the solution 28 from leaking out of the cavity 12.

Figure 1A:
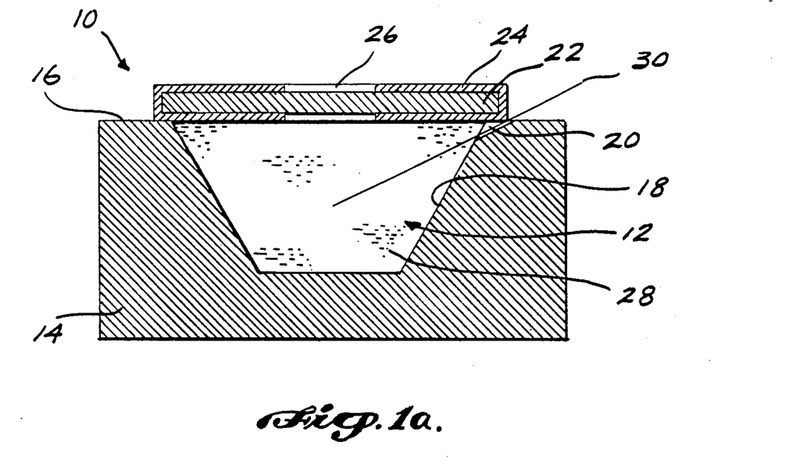
FIG. 1A is a cross-sectional view of a preferred embodiment of a liquid junction ion electrode formed in accordance with the present invention.
Figure 1B:
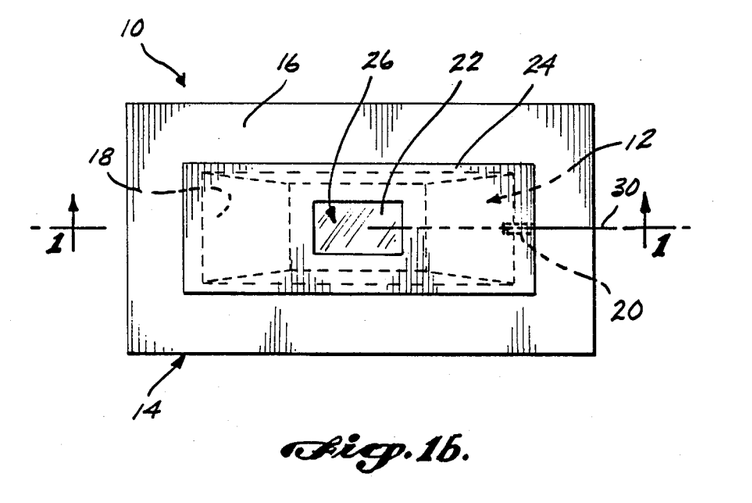
FIG. 1B is a top view of the liquid junction ion electrode of FIG. 1A.

If the ion electrode 10 is to be used as a reference electrode, the glass membrane 22 will be formed form a porous glass, having a preferable pore size in the range of 40 angstroms to 75 angstroms. The primary solution 28 will generally be saturated potassium chloride. Corning 7930 glass manufactured by Corning Glass Works in Corning, N.Y., has been successfully used as the porous glass membrane 22, and Corning 7740 glass containing mobile ions has been found suitable for the coating 24. In the case of an ion-sensitive electrode an ionsensitive glass may be used for the membrane, or the pores of the porous glass membrane may be filled with an ion-sensitive material. A suitable solution will be used to detect the activity of a predetermined ion. The electrical conductor 30 will typically be silver/silver chloride.

Figure 2:
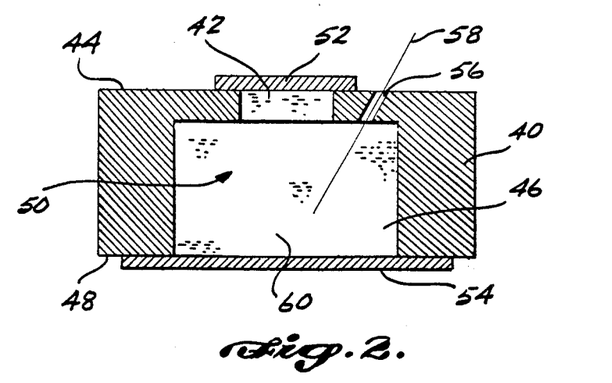
FIG. 2 is a cross-sectional view of one alternative embodiment of a liquid junction ion electrode.

FIG. 2 illustrates one alternative embodiment of the present invention wherein the body 40 has a first cavity 42 opening to an exterior surface 44 of the body 40 and a second cavity 46 opening to a second exterior surface 48 of the body 40. The first cavity 42 and the second cavity 46 communicate to form a larger single cavity 50 in the interior of the body 40. A glass membrane 52, formed of either porous glass or ion-sensitive glass, substantially covers the opening of the first cavity and is attached directly to the first exterior surface 44 by means of any suitable epoxy. An electrically nonconductive cover 54 substantially covers the opening of the second cavity 46, and it likewise may be attached to the second exterior surface 48 by means of any suitable adhesive. A channel 56 is formed in the body 40 between the first exterior surface 44 and the larger single cavity 50. Passing through the channel is an electrical conductor 58, typically a silver wire coated with silver chloride, that makes contact with the primary solution 60. After assembly, the channel 56 will be sealed to prevent the primary solution 60 from leaking out.

Figure 3:
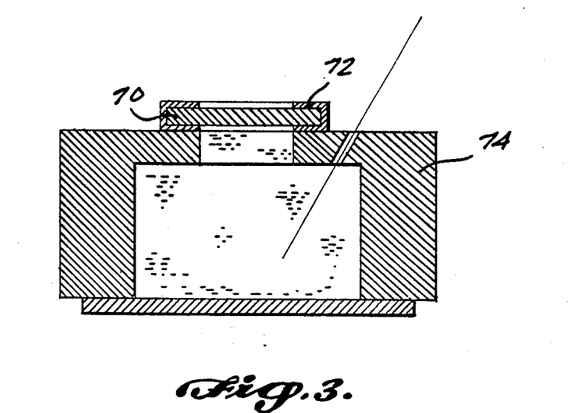
FIG. 3 is a cross-sectional view of one alternative embodiment of the liquid junction ion electrode.

FIG. 3 is an alternative embodiment of the ion electrode of FIG. 2, wherein the glass membrane 70 is formed of porous glass having a preferable pore size in the range of 40 to 75 angstroms. The glass membrane 70 has a partial coating 72 of glass containing mobile ions. The coating 72 attaches to the body 74 and provides a leak-proof seal between the body 74 and the glass membrane 70.

Figure 4:
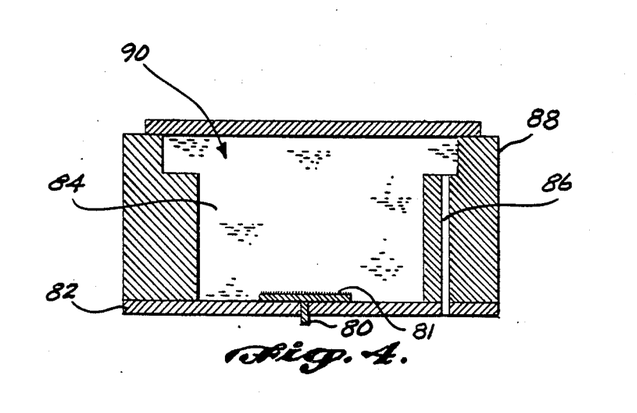
FIG. 4 is a cross-sectional view of a second alternative embodiment of the liquid junction ion electrode.

Another alternative embodiment of the invention is shown in FIG. 4, wherein the electrical conductor 80, a silver wire coated with silver chloride, passes through the electrically nonconductive cover 82 to make electrical contact with a plate 81. The plate 81 preferably has a coating of silver chloride to interact with the primary solution 84. A channel 86 passes through the electrically nonconductive cover 82 and the body 88 to communicate with the cavity 90. The channel 86 is used to drain and refill the primary solution 84. A suitable plug is used to seal the channel 86.

Figure 5:
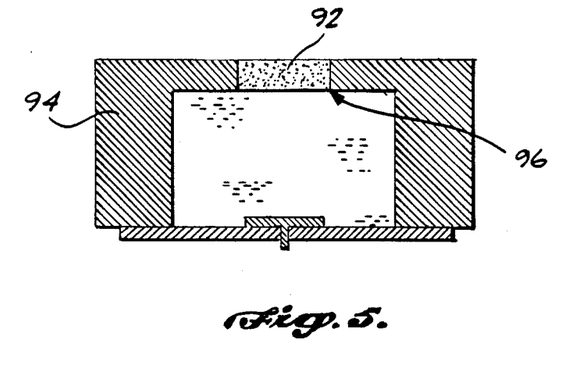
FIG. 5 is a cross-sectional view of a second alternative embodiment of a liquid junction ion electrode.
Figure 6A:
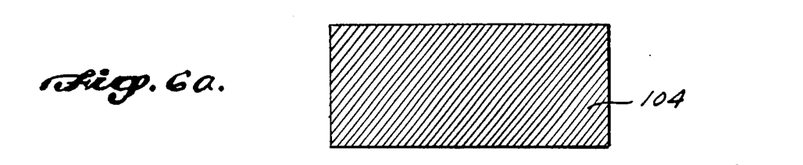
FIGS. 6A–F are cross-sectional views illustrating a preferred method of manufacturing a liquid junction ion-sensitive electrode in accordance with the present invention.
Figure 6B:
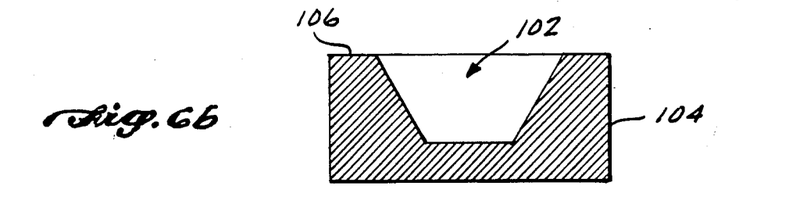
Figure 6C:
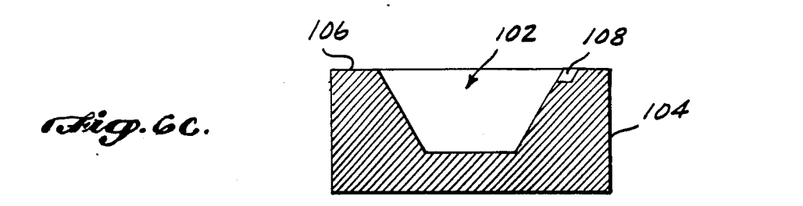
Figure 6D:
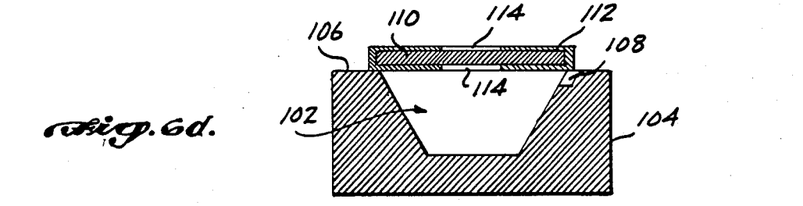
Figure 6E:
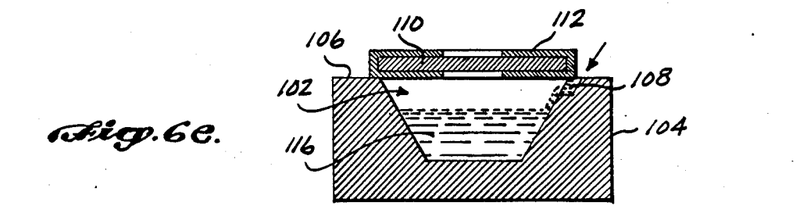
Figure 6F:
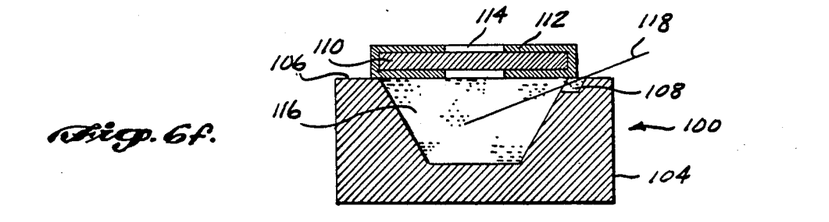
Figure 7A:
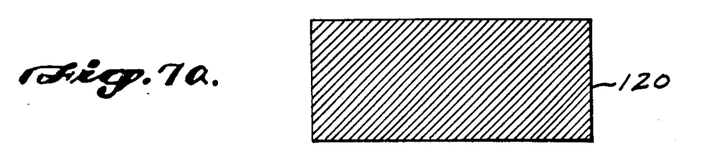
FIGS. 7A–F are cross-sectional views of a method of manufacturing a liquid junction ion electrode.
Figure 7B:
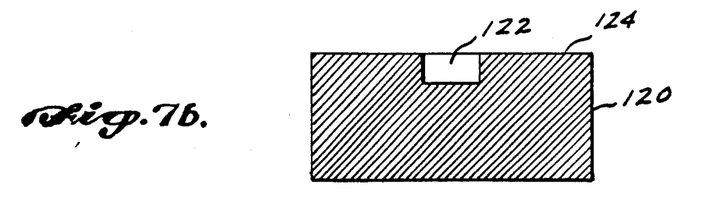
Figure 7C:
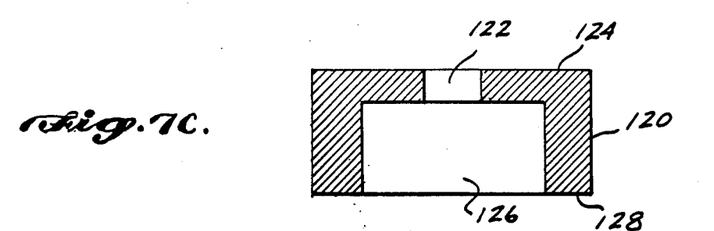
Figures 7D, 7E:
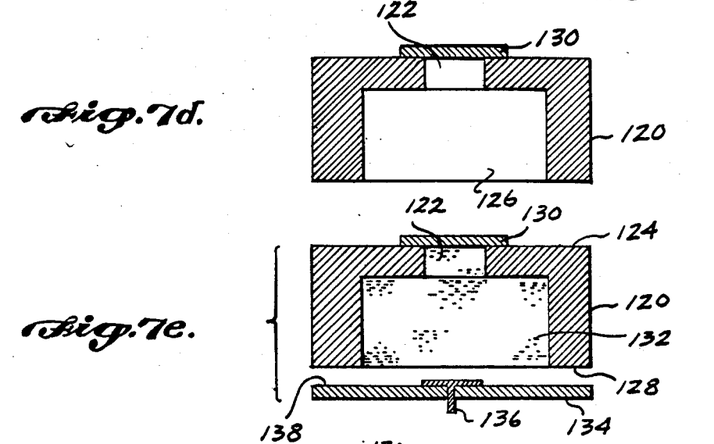
Figure 7F:
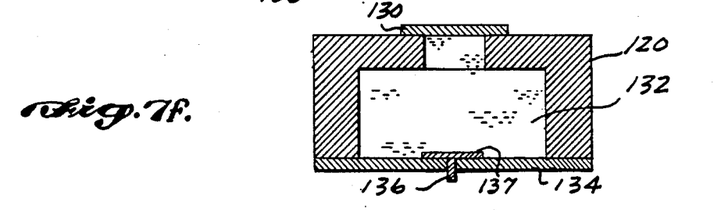
Figure 8A:
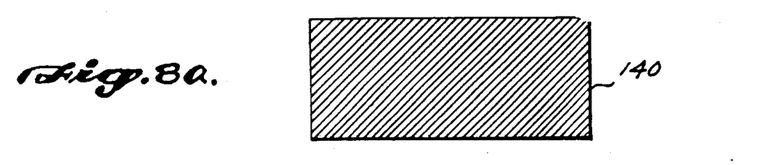
FIGS. 8A–F are cross-sectional views of an alternative method of manufacturing a liquid junction ion electrode.
Figure 8B:
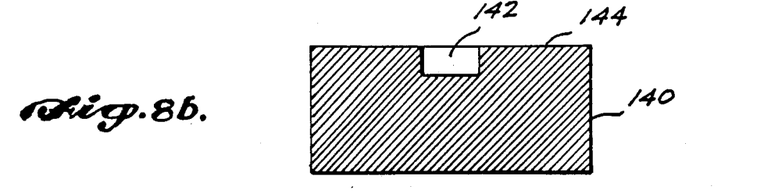
Figure 8C:
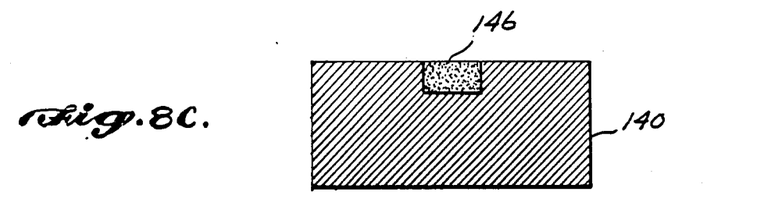
Figure 8D:
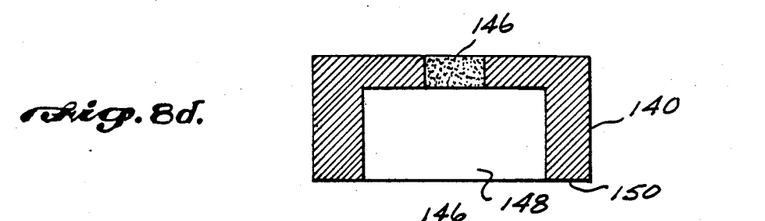
Figure 8E:
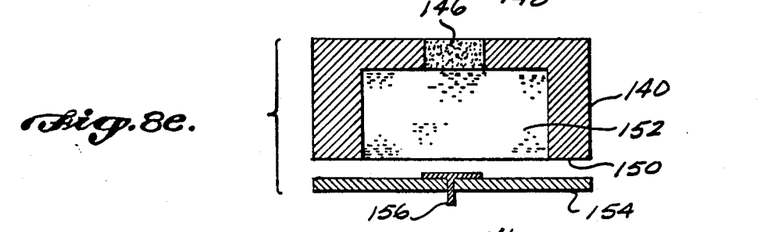
Figure 8F:
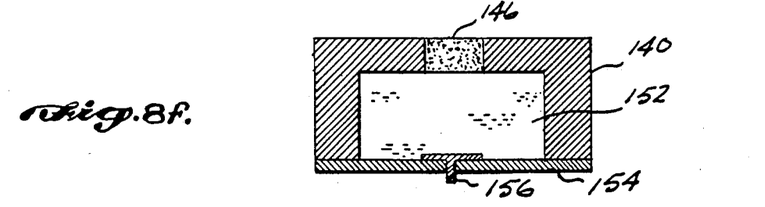

In FIG. 5 the glass membrane of the previous embodiments is replaced with a glass plug 92. The glass plug 92 is formed from a glass paste that has been subjected to high temperatures to cause pores to form in the glass plug 92. The heating process also causes the glass plug 92 to adhere to the body 94 to substantially seal the opening to the first cavity 96, thus forming a liquid junction reference electrode.

A method of manufacturing the ion electrode 100 is illustrated in FIGS. 6A-F. A cavity 102 is first created in the silicon body 104 that opens to an exterior surface 106. The cavity 102 is best created by anisotropic or isotropic chemical etching of the silicon body 104. A small passageway 108 is then formed, preferably by etching, in the silicon body 104 between the cavity 102 and the exterior surface 106.

In manufacturing a reference electrode, the opening to the cavity 102 will be covered with a porous glass membrane 110. The porous glass membrane 110 may be attached to the exterior surface 106 by a suitable epoxy. In accordance with a preferred method, the porous glass membrane 110 is first partially coated with a coating 112 of glass containing mobile ions. The coating 112 is preferably affixed to the porous glass membrane by sputtering, although other suitable methods may be used. A central area 114 on both sides of the porous glass membrane 110 is masked during the sputtering process to form a window in the coating 112 to permit interaction of the test solution with the primary solution 116 in the cavity 102. The porous glass membrane 110 and the coating 112 are then attached to the exterior surface 106 by electrostatic bonding. The cavity 102 is filled with the primary solution 116 through the small passageway 108, and an electrical conductor 118 is then passed through the small passageway 108 to make contact with the primary solution 116. The small passageway 108 can then be sealed by any suitable epoxy to prevent the primary solution 116 from leaking out. Alternatively, potassium chloride crystals are placed in the cavity 102, and then the cavity 102 is covered with the porous glass membrane 110. After the electrical conductor 118 is sealed in the passageway 108, the ion electrode 100 is soaked in ionized water. The water molecules pass through the porous glass membrane 110 to mix with and form the primary solution.

FIGS. 7A-F illustrate an alternative method of manufacturing the ion electrode formed in accordance with the present invention. A first cavity 122 is created in the interior of the silicon body 120 by chemically etching from a first surface 124 of the body 120. A second cavity 126 is then chemically etched in the interior of the body 120 to communicate with the first cavity 122.

An ion-sensitive membrane 130 is affixed to the first surface 124 to substantially cover the opening to the first cavity 122. As described above, the ion-sensitive membrane 130 may be affixed by epoxy or it may be first coated with a glass containing mobile ions and then electrostatically bonded to the body 120. After the opening to the first cavity 122 is covered, the combined cavities are filled with a primary solution 132. An electrically nonconductive cover 134, having a plate 137 affixed to the interior surface 138, is affixed to the exterior surface 128 of the body 120 to substantially cover the opening to the second cavity 126. The electrically nonconductive cover 134 may be epoxied to the exterior surface 128, or other known methods may be used for forming a leak-proof seal. An electrical conductor 136 is passed through the cover 134 to make contact with the plate 137.

FIGS. 8A-F show still yet another alternative method of manufacturing an ion electrode in accordance with the present invention. As previously described, a first cavity 142 is created in the silicon body 140 by chemically etching from a first side 144 of the body 140. A glass paste formed of ground glass and organic binder is then placed within the cavity 142 and heated to evaporate the organic binder and form a porous glass plug 146. The porous glass plug 146 adheres to the body 140 to seal the opening to the first cavity 142. A second cavity 148 is then created in the interior of the body 140 by chemically etching from a second side 150 of the body 140. The combined cavities are then filled with a primary solution 152, and an electrically nonconductive cover 154 having an electrical conductor 156 passing therethrough is affixed to the second side 150 of the body 140 to substantially cover the opening to the second cavity 148. The porous glass plug 146 may also be formed of an ion-sensitive material to create an ion-sensitive electrode.

While preferred embodiments and various alternatives of the invention and method for manufacturing the same have been illustrated and described, it will be appreciated that various changes can be made therein without departing from the spirit and scope of the invention. for instance, the opening to one of the first or second cavities may be formed of multiple openings of one micron or less in size that are created by anisotropic etching. These openings may then be filled with an ion-sensitive material to form an ion-sensitive electrode. Consequently, the invention can be practiced otherwise than as specifically stated herein.

The embodiments of the invention in which an exclusive property or privilege is claimed are defined as follows:

1. An ion electrode for detecting the ionic concentration of a liquid, the ion electrode comprising:
   (a) a body formed of silicon having a cavity that opens into an exterior surface of said body;
   (b) a glass membrane attached to said body to substantially cover said cavity opening, said glass membrane being partially coated with a glass material containing mobile ion that attaches said glass membrane to said exterior surface of said body;
   (c) a chemical solution in said cavity, said solution filling enough of said cavity to be in contact with said glass membrane; and
   (d) electrical conducting means passing through said body between said cavity and the exerior of said body to make contact with said solution.

2. The ion electrode of claim 1, wherein said glass membrane comprises porous glass having a pore size in the range of 40 angstroms to 75 angstroms.

3. The ion electrode of claim 1, wherein said glass membrane is formed of an ion-sensitive glass.

4. The ion electrode of claim 1, wherein said glass membrane is formed of porous glass having ion-sensitive material filling each pore.

5. The ion electrode of claim 1, wherein:
   (a) said cavity opens into two surfaces of said body, one of said openings is covered by said glass membrane, and
   (b) the ion electrode further comprises a cover formed of an electrically nonconductive material and attached to said body to cover the other of said openings in said body.

6. The ion electrode of claim 5, wherein said glass membrane comprises porous glass having a pore size in the range of 40 angstroms to 75 angstroms.

7. The ion electrode of claim 5, wherein said glass membrane is formed of porous glass having ion-sensitive material filling said pores.

8. The ion electrode of claim 5, wherein said electrical conducting means passes through said cover.

9. The ion electrode of claim 8, wherein sid electrical conducting means comprises:
   (a) a plate affixed to an interior side of said cover, said plate having a coating of silver chloride; and
   (b) an electrical conductor attached to said plate that passes through said cover to the exterior of said cover.

10. The ion electrode of claim 5, further comprising a channel formed in said body for filling and draining said solution in said cavity.

11. The ion electrode of claim 10, wherein said glass membrane is formed of an ion-sensitive glass.

12. A method of manufacturing an ion electrode, comprising the stpes of:
   (a) creating a cavity in a silicon body that opens to an exterior surface of said body;
   (b) forming a small passageway in said body between said cavity and said exterior body;
   (c) covering said opening with a glass membrane;
   (d) filling said cavity with solution through said small passageway in said body; and
   (e) passing a chemically coated electrical conductor through said small passageway so that said electrical conductor is in contact with said solution.

13. The method of claim 12, wherein the step of creating a cavity comprises chemically etching said cavity in said body.

14. The method of claim 13, wherein the step of covering said opening comprises bonding said glass membrane to said body with an epoxy adhesive.

15. The method of claim 13, wherein the step of covering said opening further comprises:
   (a) forming said glass membrane of a porous glass material;
   (b) partially covering said glass membrane with a coating of glass containing mobile ions; and
   (c) affixing said glass membrane to said silicon body by the process of electrostatically bonding said glass containing mobile ions to said body.

16. The method of claim 15, wherein the step of partially covering said glass membrane comprises sputtering on the glass containing mobile ions to said porous glass membrane.

17. The method of claim 15, wherein the step of partially covering said glass membrane further comprises the steps of filling the pores with an ion-sensitive material and sputtering on the glass containing mobile ions to said glass membrane.

18. The method of claim 12, wherein the step of creating a cavity comprises:
   (a) creating a first cavity in the interior of said body by chemicallly etching from a first side of said body;
   (b) creating a second cavity in the interior of said body by chemically etching a second side of said body, said second cavity opening to a second exterior surface of said body and communicating with said first cavity to create a larger single cavity;
   (c) covering one of said openings with a glass membrane; and
   (d) covering the second of said openings with an electrically nonconductive cover.

19. The method of claim 18, wherein the step of covering one of said openings with a glass membrane further comprises:
   (i) forming said glass membrane of a porous glass material;
   (ii) partially covering said glass membrane with a coating of glass containing mobile ions; and
   (iii) affixing said glass membrane to said silicon body by the process of electrostatically bonding said glass containing mobile ions to said body.

20. The method of claim 19, wherein the step of partially covering said porous glass membrane further comprises a sputtering said glass containing mobile ions onto said glass membrane.

21. The method of claim 19, wherein the step of partially covering said porous glass membrane comprises the steps of filling said pores with ion-sensitive material and sputtering said glass containing mobile ions onto said glass membrane.

22. The method of claim 18, wherein said step of covering one of said openings comprises bonding said glass membrane to said body with an epoxy adhesive.

23. The method of claim 18, wherein the step of covering one of said openings with a glass membrane further comprises:
   (i) grinding a glass material to a powder form;
   (ii) combining said powder with an organic binder to form a glass paste;
   (iii) applying said glass paste to fill said first cavity; and
   (iv) evaporating said organic binders out of said glass paste to form a porous glass plug that plugs the opening of said cavity.

24. A method of manufacturing an ion electrode, comprising the steps of:
   (a) creating a first cavity in the interior of a silicon body by chemically etching from a first side of said body;
   (b) sealing said cavity by:
      (i) grinding a glass material to a powder form;
      (ii) combining said powder with an organic binder to form a glass paste;
      (iii) applying said glass paste to said first cavity; and
      (iv) evaporating said organic binder out of said glass paste to form a porous glass plug;
   (c) creating a second cavity in the interior of said body by chemically etching a second side of said body, said second cavity opening to a second exterior surface of said body and communicating with said first cavity to create a larger single cavity;
   (d) filling said larger single cavity with a solution; and (e) covering said second opening with an electrically nonconductive cover having a chemically coated electrical conductor passing therethrough to contact said solution.

25. A method of manufacturing an ion electrode, comprising the steps of:
   (a) creating a first cavity in the interior of a silicon body that communicates with an exterior surface of said body by chemically etching from a first side of said body;
   (b) creating a second cavity in the interior of said body by chemically etching a second side of said body, said second cavity opening to a second exterior surface of said body and communicating with said first cavity to create a larger single cavity;
   (c) covering one of said openings with a glass membrane;
   (d) filling said cavity with a solution; and
   (e) covering said second opening with an electrically nonconductive cover having a chemically coated electrical conductor passing therethrough to contact said solution.

26. The method of claim 25, wherein the step of covering one of said openings with a glass membrane further comprises the step of filling the pores with an ion-sensitive material.

27. A method of manufacturing an ion electrode, comprising the steps of:
   (a) creating a cavity in a silicon body that opens to an exterior surface of said body;
   (b) forming a small passageway in said body between said cavity and said exterior surface;
   (c) placing potassium chloride crystals in said cavity;
   (d) covering said opening with a porous glass membrane;
   (e) passing a chemically coated electrical conductor through said small pasageway so that said electrical conductor is extending into said cavity; and
   (f) soaking said silicon body in ionized water so that the water molecules in said ionized water pass through said porous glass membrane and mix with said potassium chloride crystals to thereby fill said cavity with a solution.

28. An ion electrode for detecting the ionic concentration of a liquid, the ion electrode comprising:
   (a) a body formed of silicon having a cavity that opens into two surfaces of said body;
   (b) a glass membrane formed from a glass paste that plugs one of said cavity openings;
   (c) a cover formed of an electrically nonconductive material and attached to said body to cover the other of said openings in said body;
   (d) a chemical solution in said cavity, said solution filling enough of said cavity to be in contact with said glass membrane; and,
   (e) electrical conducting means passing into said cavity to make contact with said solution.

29. The ion electrode of claim 28, wherein said glass paste forms a porous glass plug having a pore size in the range of 40 angstroms to 75 angstroms.

30. The ion electrode of claim 28, wherein said glass paste is formed of an ion-sensitive material.

31. The ion electrode of claim 28, wherein said electrical conducting means comprises:
   (i) a plate affixed to an interior side of said cover, said plate having a coating of silver chloride; and,
   (ii) an electrical conductor attached to said plate and passing through said cover to the exterior of said cover.

32. The ion electrode of claim 28, further comprising a channel formed in said body for filling and draining said solution in said cavity.

* * * * *